United States Patent [19]

El Shami et al.

[11] Patent Number: 4,778,751

[45] Date of Patent: Oct. 18, 1988

[54] METHOD FOR MEASURING ANTIGENS OR ANTIBODIES IN BIOLOGICAL FLUIDS USING LIGAND LABELED ANTIGENS OR LIGAND LABELED ANTIBODIES

[75] Inventors: A. Said El Shami, Agoura Hills; Olusola O. Alaba, Pasadena; Charles A. Kasal, South Pasadena, all of Calif.

[73] Assignee: Diagnostic Products Corporation, Los Angeles, Calif.

[21] Appl. No.: 862,123

[22] Filed: May 12, 1986

[51] Int. Cl.⁴ .................. G01N 53/00; G01N 33/537
[52] U.S. Cl. ........................ 435/7; 435/805; 436/504; 436/513; 436/527; 436/532; 436/538; 436/539; 436/541; 436/542; 436/823
[58] Field of Search ............ 435/7, 805; 436/501, 436/503, 504, 513, 527, 532, 538, 539, 541, 542, 823

[56] References Cited

U.S. PATENT DOCUMENTS

| 4,281,061 | 7/1981 | Zuk et al. ............... 436/537 X |
| 4,343,896 | 8/1982 | Wolters et al. ............ 436/540 X |
| 4,401,764 | 8/1983 | Smith ...................... 436/532 X |
| 4,495,296 | 1/1985 | Neurath et al. ........... 436/543 X |
| 4,506,009 | 3/1985 | Leuhoff et al. ........... 436/538 X |
| 4,508,830 | 4/1985 | Baker et al. ............. 436/532 X |
| 4,522,922 | 6/1985 | Carro et al. ............. 436/538 X |
| 4,530,900 | 7/1985 | Marshall ................. 436/538 X |
| 4,595,661 | 6/1986 | Cragle et al. ............ 436/538 X |

*Primary Examiner*—Robert J. Warden
*Assistant Examiner*—Richard Wagner
*Attorney, Agent, or Firm*—Joseph E. Mueth

[57] ABSTRACT

The method of measuring circulating antigens or antibodies by using a ligand labeled specific antigen or ligand labeled specific antibody chemically attached to a soluble matrix or backbone, a differently labeled anti-antigen or anti-antibody and a solid phase anti-ligand directed at the ligand attached to the specific antigen or specific antibody. This is achieved by either one or two analytical schemes:

(a) Reacting a patient sample with a ligand labeled specific antigen or a ligand labeled specific antibody in the liquid phase in the presence of a differently labeled specific anti-antigen or labeled specific anti-antibody. This immunological complex is reacted with an immobilized anti-ligand on a solid support which is directed against the ligand attached to the specific antigen or antibody through the liquid matrix. Subsequently the solid phase is washed and checked for the label on the anti-antigen or anti-antibody which is directly proportional to the concentration of specific antigen or antibody.

(b) Reacting a patient sample with the ligand labeled specific antigen or a ligand labeled specific antibody in the liquid phase, then contacting said liquid phase with an immobilized anti-ligand on a solid support; washing the solid support and reacting it with a differently labeled anti-antigen or anti-antibody. This is followed by re-washing of the solid support and checking for the presence of the label attached to the anti-antigen or anti-antibody which is directly proportional to the concentration of the specific antigen or antibody. The ligand is covalently attached to the specific antigen or antibody through a soluble liquid matrix or backbone to which the specific antigen or antibody has been chemically attached. This invention is applicable to a wide variety of antigen or antibody detection as described herein.

14 Claims, No Drawings

METHOD FOR MEASURING ANTIGENS OR ANTIBODIES IN BIOLOGICAL FLUIDS USING LIGAND LABELED ANTIGENS OR LIGAND LABELED ANTIBODIES

BACKGROUND OF THE INVENTION

Liquid phase and solid phase immunoassays and their numerous modifications and variations have been described in the literature for the measurement of a host of circulating antigens and antibodies. Numerous U.S. and Foreign patents have been issued dealing with one or more aspects of immunoassay techniques.

Competitive isotopic double antibody separation immunoassay techniques have played a substantial role in the measurement of antigens and haptens. Such methods are sensitive and reproducible but require centrifugation to separate the free labeled antigen or hapten from the antibody bound label. Although such methods utilize first order liquid phase kinetics, they rely on polyethylene glycol catalyzed second antibody separation. Several drawbacks are inherent in such systems; namely, (a) the stringent requirement of a highly purified antigen or hapten for isotopic labeling and (b) high nonspecific binding due in part to tracer impurity and instability and/or polyethylene glycol-second antibody separation.

Competitive enzyme double antibody separation immunoassay techniques have been used on a much smaller scale. Antigen or hapten enzyme labels, although more stable than their isotopic counterparts, suffer in such assays due to extremely high nonspecific bindings and require multiple washings thus reducing sensitivity and reproducibility.

Substituting fluorescent or chemiluminescent labels in said double antibody competitive type assays have not fully resolved the intrinsic problem of non-specific binding and limited sensitivity and reproducibility of such methods. Homogeneous enzyme immunoassays as described in U.S. Pat. No. 3,817,837 have in part addressed the non-specific binding problem described above for non-isotopic competitive double antibody separation techniques. However, the teachings of said U.S. Pat. No. 3,817,837 are limited to small molecular weight haptens that are present in fairly high concentrations in body fluids.

Fluorescent polarization competitive immunoassay as described in U.S. Pat. No. 4,420,568 has successfully eliminated most of the sensitivity problems described in U.S. Pat. No. 3,817,837 but so far their applications have been limited to small molecules. Other competitive fluorescent immunoassays have since been reported for large molecular weight antigens but like fluorescent polarization require a special dedicated instrument for their practice.

Competitive solid phase immunoassays have been in use for the past decade and have gradually replaced competitive double antibody separation techniques for small molecular weight haptens and several larger antigens with a molecular mass of less than 30,000 daltons. Such isotopic competitive solid phase immunoassays are virtually free of non-specific binding problems associated with liquid phase competitive immunoassays but are not applicable to large molecular weight antigens due mainly in part to steric hindrance on the solid support.

Solid phase non-isotopic competitive immunoassays suffer from similar problems of steric hindrance on the solid support and in case of enzyme labels the size of the label itself adds to steric problem as well. The present invention will address some of the steric hindrance problems of solid phase supports inherent in competitive solid phase assays. Solid phase immunometric isotopic and non-isotopic assays have been well developed for the measurement of large molecular mass polyvalent antigens and antibodies. Several methods have been published and lately several U.S. and Foreign patents have been issued describing different aspects of this analytical technique.

U.S. Pat. No. 3,654,090 was one of the earliest teachings of a sequential two-step immuno-enzymometric assay for the detection of polyvalent antigens. Several modifications of the original teachings of said patent have since been applied to the measurement of high molecular mass antigens using either isotropic or non-isotopic signal producing probes.

For obvious analytical reasons it is well established that the use of two different polyclonal antibodies raised in different species directed at the same antigen (one immobilized on solid support and the second labeled with a signal producing probe) enhances the sensitivity of the assay and reduces to a certain extent background signals in immunometric assays. U.S. Pat. No. 4,376,110 teaches the use of two monoclonal antibodies directed at two different epitopes on polyvalent antigens in immunometric assays. Unlike U.S. Pat. No. 3,654,090, U.S. Pat. No. 4,376,110 uses a co-incubation non-sequential assay system. Similarly, U.S. Pat. No. 4,474,892 also describes a two-site immunometric assay system using monoclonal antibodies of different classes or subclasses directed at the same antigen. The above-described methods although they achieve acceptable sensitivity, specificity and to a certain extend reduced background signals, all suffer from low reaction kinetics due to the immobilization of the antibody on solid support and a solid phase type reaction. It is well established that solid phase reactions have lower reaction kinetics than liquid phase reactions and also have lower signal to background ratio even if the immobilized antibody has a higher affinity constant prior to immobilization. This is largely due to steric hindrance effects on the solid support. If such methods are not properly optimized in so far as the quantity of immobilized antibody and the concentration and specific activity of the probe producing signal attached to the second antibody are concerned, the so-called "high-dose hook effect" could jeopardize the reliability and validity of such methods.

A further disadvantage of immunometric methods is the inconsistency of the antibody immobolizing process from batch to batch. U.S. Pat. No. 4,496,654 discloses this problem of inconsistent immobilization of antibodies and teaches that by first immobilizing avidin on a solid support then reacting said support with biotinylated antibody to form a solid phase antibody support, uniform immobilization is achieved. However, in this disclosed modification slower reaction kinetics are inevitable and the dangers of a "high-dose hook effect" are still probable. The present invention addresses these shortcomings and the disadvantages inherent in these immunometric assays.

Modifications of classical immunometric assays for the detection of antigens has also been extended for the measurement of specific antibodies by using immobilized antigens as the immunosorbant. A notable application of such techniques has been widely used for the detection of allergen specific immunoglobulins, IgE (reagin-immunoglobulins). Historically, specific allergen testing has followed the teachings of U.S. Pat. No. 3,720,760 and its Foreign counterparts, in which specific allergens are immobilized on a solid support (mainly filter paper discs) and reacted with a patient sample suspect of containing the allergen specific immunoglobulin IgE. After an initial incubation (typically 24 hours) the solid support is washed to remove any non-specific binding from the serum components, then the solid support is allowed to react with a labeled anti-IgE antibody. After a second wash step of the solid support it is checked for the presence of labeled material. This approach, although widely used has several shortcomings; namely, slow reaction kinetics due to the solid phase reactions, difficulty of producing immobilized allergens that have the same binding characteristics as the natural allergens for IgE and the inconsistency of producing a solid phase allergen from batch to batch.

Recently, Aalberse, et al. (J. Imm. Methods 87: 51–57 (1986)) decribe the use of hapten-modified antigens instead of solid phase coupled antigens in a radioallergosorbent test-type assay. In such assay a patient sample suspected of containing specific allergen IgE is reacted with trinitrobenzene sulfonic acid (TNP) modified specific allergen for two hours then further reacted overnight with a solid phase coupled anti-TNP to form IgE-allergen-TNP-anti-TNP complex. The solid phase is washed and again reacted overnight with 125-I-anti-IgE antibody, rewashed and counted for the presence of 125-I isotope which is directly proportional to the concentration of allergen specific IgE in the patient sample. In this approach the authors claim to have gained the benefit of liquid phase kinetics in their first reaction but fail to substantiate the extent of TNP labeling of their allergens. Directly labeling allergens with haptens such as TNP poses the problem of missing certain vital allergenic components that might not be labeled during such a process and thus will not be quantified in said process. Also, the authors failed to show enhanced reaction timing (two days) as compared to the method described in U.S. Pat. No. 3,720,760.

The present invention circumvents the problems associated with the traditional method of allergen testing and the modifications thereof.

SUMMARY OF THE INVENTION

The present invention concerns itself with the measurement of circulating antigens or antibodies in biological fluids using a novel approach. This approach described herein makes use of a specific antigen or antibody chemically attached to a soluble matrix or backbone which is subsequently labeled with a given ligand. After an initial liquid phase reaction with a patient sample, the immunocomplex formed between the patient antigen or antibody and an anti-antigen or anti-antibody labeled with a signal producing probe is immobilized in situ on a solid support containing an anti-ligand directed at the ligand attached to the liquid matrix. This approach of attaching antigens of antibodies to a liquid soluble matrix which is subsequently labeled with a given ligand serves at least two distinct purposes:

(a) it increases the potential number of immunocomplexes that could be immobilized on a solid support through an anti-ligand since only few ligands need to be attached to the liquid matrix to effect complete immobilization of the entire immunocomplex. Direct labeling of antigens or antibodies with a given ligand without the use of a liquid matrix as described herein would limit the number of immunocomplexes to be immobilized on the solid support by an anti-ligand since the chances are that only a few antigens or antibodies would be labeled with a given ligand and that would require the use of elaborate affinity chromatographic techniques to separate the ligand labeled antigens or antibodies from the unlabeled antigens or antibodies.

(b) the benefits of using liquid phase kinetics in the first reaction are obvious since this facilitates the formation of the immumocomplex between the antigens or antibodies attached to the liquid matrix and the signal producing labeled anti-antigen or anti-antibody.

If liquid phase kinetics are not sought, the teachings of this invention could be used to prepare efficient solid phase matrices by attaching antigens or antibodies to a liquid matrix and labeling said matrix with a given ligand then pre-reacting said matrix with a solid phase support containing an anti-ligand.

DETAILED DESCRIPTION OF THE INVENTION

Several analytical schemes are described in this invention.

Scheme I: Non-Sequential Assay:

A patient sample suspected of containing a given antigen or antibody is allowed to react in the liquid phase with the liquid matrix containing the labeled ligand-antibody or the labeled-ligand antigen in the presence of a differently labeled specific anti-antibody or labeled specific anti-antigen. This immunological complex in the liquid phase is reacted with an anti-ligand immobilized on a solid support which is directed against the ligand attached to specific antigen or antibody through the liquid matrix. The solid phase is then washed and checked for the label producing signal attached to the anti-antigen or the anti-antibody. This can be shown graphically for the detection of antigens or antibodies as follows:

(a) Antibody Detection Non-Sequential Assay:

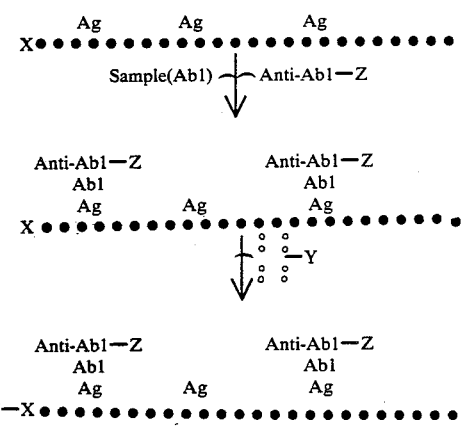

Wash and check for Z.
Where
Ab1 = circulating antibody to be measured.
Ag = specific antigen directed against Ab1 attached covalently to liquid matrix.
X = ligand covalently attached to liquid matrix.
Y = anti-ligand covalently or passively attached to solid support.

Z = signal producing label (enzyme, radioactive label, fluorescent chemiluminescent compound, bioluminesnt compound, or an enzyme substrate).

• • • • • = the liquid matrix.

The concentration of antibody Ab1 is directly proportional to the signal produced by Z.

(b) Antigen Detection Non-Sequential:

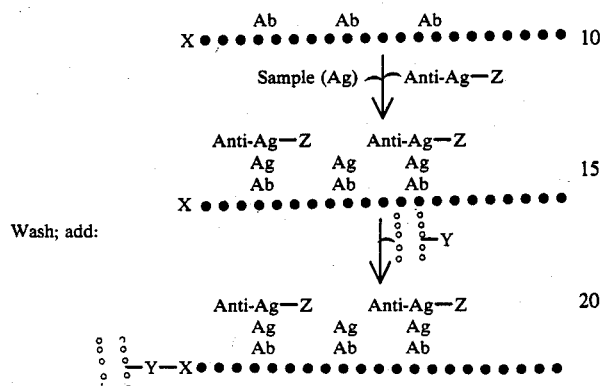

Rewash solid phase and check for Z where the concentration of circulating Ag is directly proportional to the signal produced by Z.

Scheme II: Sequential Assays:

In sequential assays the patient sample is reacted with ligand labeled specific antigen or antibody in the liquid phase then contacted with the solid phase anti-ligand and allowed to react for a specific amount of time. The solid phase is subsequently washed and re-reacted with an anti-antigen or anti-antibody labeled with a signal producing probe. The solid phase is rewashed and checked for the signal producing probe.

The following is the diagramatical presentation of such concept:

(a) Antibody Detection Sequential Assays:

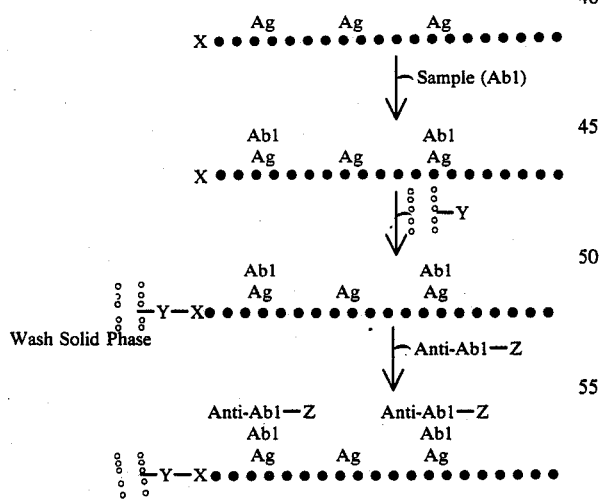

Wash solid phase and check for Z.

(b) Antigen Detection Sequential Assay:

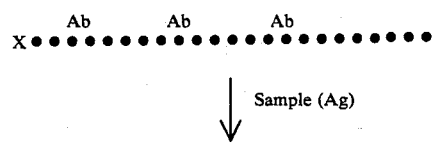

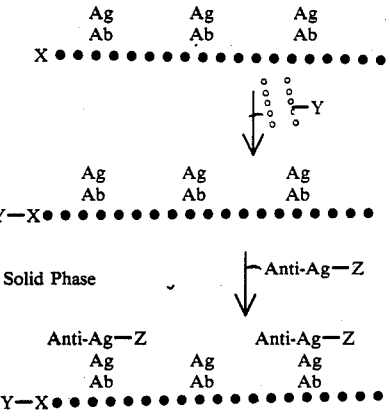

Wash solid phase and check for Z.

Scheme III: Hapten Detection; Competitive Assays:

In case of hapten detection a specific antibody to a given hapten under consideration is chemically attached to a soluble liquid matrix or backbone and subsequently labeled with a ligand. A patient sample suspected of containing said hapten is allowed to react in the liquid phase with the soluble matrix containing the ligand labeled specific antibody in the presence of a hapten labeled probe (H-Z) as depicted below. Competition occurs between the patient hapten and the labeled hapten probe for binding sites on the ligand labeled antibody for a given amount of time. This is followed by addition of an immobilized anti-ligand on a solid support directed against the ligand attached to the soluble matrix containing the specific antibody. The solid phase is washed and checked for the presence of the hapten labeled probe which is inversely proportional to the concentration of hapten in the patient sample.

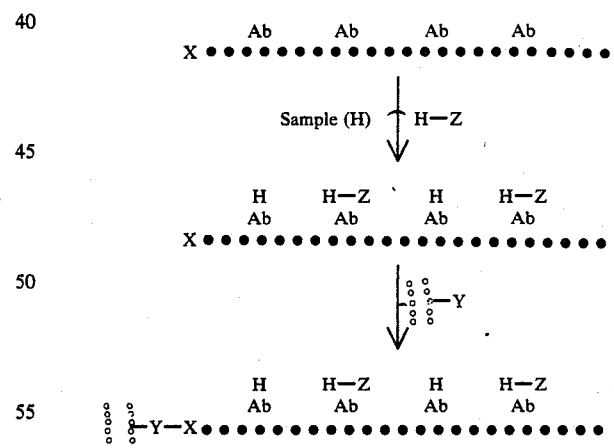

Wash solid phase and check for Z.

For certain haptens it might be beneficial to attach the ligand directly to the hapten specific antibody without the use of a soluble liquid matrix to avoid possible steric hindrance if the hapten labeled signal producing probe is of a large molecular mass especially certain enzyme labels.

The use of a soluble liquid matrix or backbone for attaching specific antigen or antibodies and the subsequent labeling of said backbone with a given ligand is the preferred embodiment of this invention. Variations in the mode or sequence of attachments to said matrix will be obvious to those skilled in the art.

PREPARATION OF SOLUBLE ANTIGEN OR ANTIBODY LIQUID MATRIX

The following reaction sets describe different reaction schemes for preparing soluble matrices or backbones containing a given antigen or antibody and a specific ligand. In these sets of reactions soluble polymers are activated with different compounds and reacted by different mechanisms. The activated polymer matrices are either covalently coupled directly with an antigen or antibody or indirectly through a polypeptide polymer or copolymer to which an antigen or antibody is then covalently attached. The matrix-antigen or antibody complex or matrix-polypeptide/copolymer-antigen or antibody complex is then labeled with a ligand directly or indirectly through a previously labeled ligand leash. The ligand used in these examples is biotin and the anti-ligand is avidin. For other possible ligand-anti-ligand combinations refer to section on possible other ligands.

REACTION SCHEME 1

Two soluble carbohydrates are utilized in this reaction sequence: (i) soluble dextran with a molecular mass varying from 6,000 to 80,000 daltons and (ii) soluble Ficoll with a molecular mass varying from 70,000 to 400,000 daltons. These two carbohydrates are used in the following examples and are abbreviated MATRIX-OH. The amino acid copolymers used in the following examples could be selected from a number of such copolymers examples of which are (a) polylysine, phenylalanine (b) polylysine, alanine (c) polyglutamic, glutamic ester or (d) polyglutamic, alanine, lysine, tyrosine. Other amino acid copolymers will be obvious to those skilled in the art.

REACTION SEQUENCE 1a 1,1'-carbonyldiimidazol (CDI) Activation and Coupling

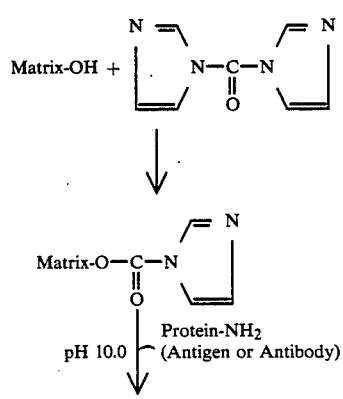

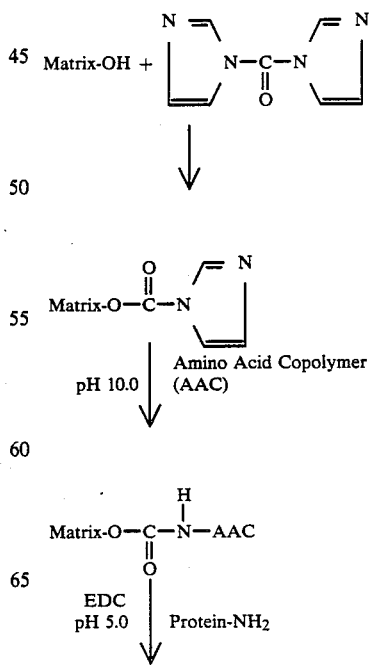

*EDC is N—ethyl-N—(3-dimethylaminopropyl) carbodiimide.

REACTION SEQUENCE 1b

Use of Amino Acid Copolymer with CDI Reaction

-continued

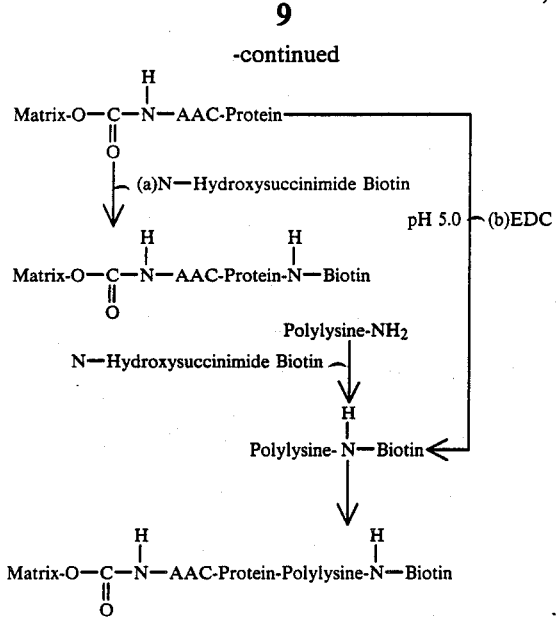

The following Examples are presented solely for purposes of illustration.

EXAMPLE 1

Preparation of Matrix Containing Specific Allergens Using Reaction Sequence 1b

The above CDI activation reaction as modified from Bethell, G., et al J. Biol. Chem. 254: 2572 (1979) was applied to the preparation of specific allergens using Reaction Sequence 1b and described herein:

(i) 124 nM of Matrix-OH as described under Reaction Sequence 1, supra, was dissolved in 2.0 mls of dimethyl sulfoxide containing 10.0 mg of 1,1'-carbonyldiimidazol (CDI) and reacted at ambient temperature for 30 minutes with frequent shaking.

(ii) 770 nM of amino acid copolymer (eg. glutamic acid, ethyl glutamate) dissolved in 2.0 mls of dimethyl-sulfoxide were added to the reaction mixture in (i) above and allowed to react for 24 hours at ambient temperature while shaking.

(iii) The reaction mixture from (i) and (ii) above was diluted with 2 volumes of water and chromatographed on Sepharcryl-300 column to isolate the Matrix-copolymer complex.

(iv) Fractions containing the Matrix-copolymer were dialyzed against distilled water and further dialyzed against acetate buffer pH 5.0.

(v) To the dialyzed Matrix-copolymer conjugate 20.0 mg of lyophilized allergen extract was added following by the addition of 0.15M N-ethyl-N'-(3-dimethylaminopropyl)carbodiimide (EDC) and allowed to react for 24 hours at 4 degrees centigrade while shaking. The pH of the reaction was maintained at pH 5.0 during this reaction period. The reaction mixture was then dialyzed versus 0.1M sodium bicarbonate buffer at pH 8.1 for 12 hours at 4 degrees centigrade.

(vi) The Matrix-copolymer-allergen conjugate was further reacted with 7.3 uM of N-hydroxysuccinimide biotin dissolved in 1.0 ml of dimethylformamide overnight at 4 degrees centigrade. The final reaction mixture was chromatographed on a Sephacryl-300 column and the fractions corresponding to the Matrix-copolymer-allergen-biotin conjugate were pooled and checked for allergen activity as detailed below.

Alternatively, the above reaction was modified where biotinylated polylysine was reacted with the Matrix-copolymer-allergen conjugate in step (vi) above as follows: 1.8 uM of polylysine (molecular mass 3,800 daltons) and 180 uM of N-hydroxysuccinimide biotin were dissolved in 1.0 ml of dimethylformamide and allowed to react for 4 hours at ambient temperature. The biotinylated polylysine was chromatographed on a CM-Sepharose column and eluted with 50 mM sodium borate pH 9.0 containing 2.0M sodium chloride. The biotinylated polylysine conjugate was adjusted to pH 5.0 and reacted with the Matrix-copolymer-allergen conjugate using EDC as described under (vi) and chromatographed to yield Matrix-copolymer-allergen-polylysine-biotin conjugate.

REACTION SEQUENCE 2a

Cyanogen Bromide Activation and Coupling

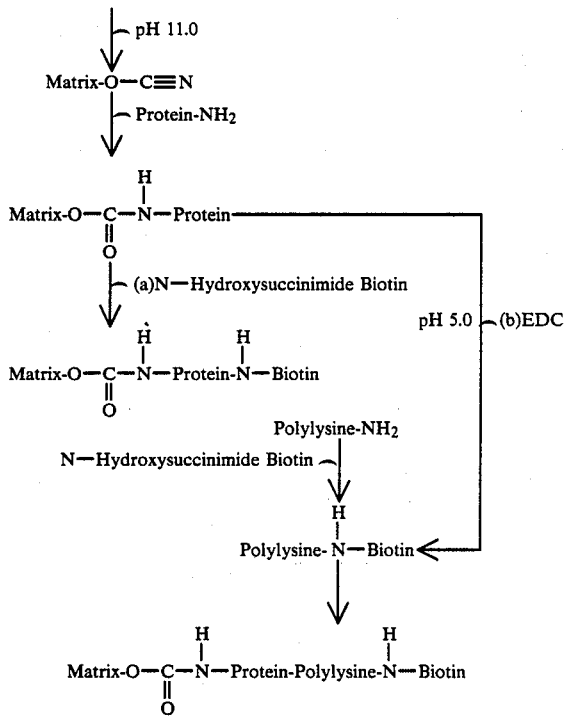

REACTION SEQUENCE 2b

Use of Amino Acid Copolymer (ACC) with Cyanogen Bromide Reaction

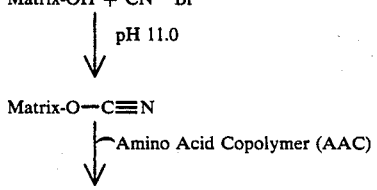

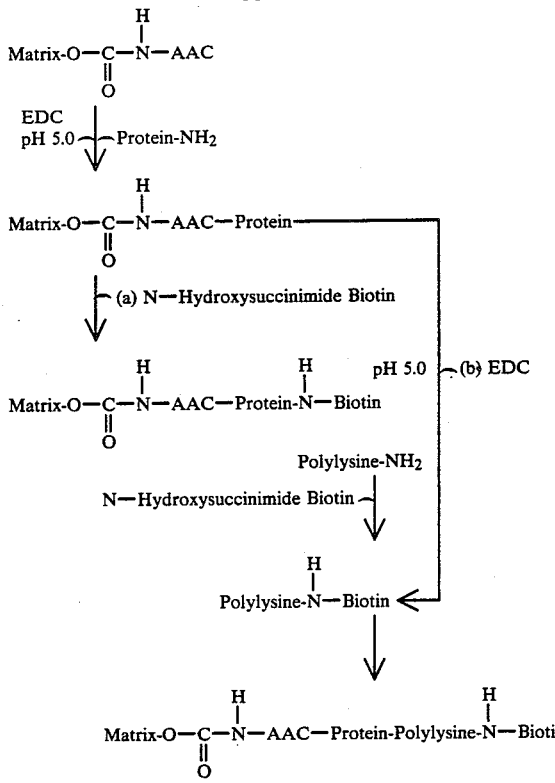

EXAMPLE 2

PREPARATION OF MATRIX CONTAINING SPECIFIC ALLERGENS USING REACTION SEQUENCE 2b

The above cyanogen bromide activation reaction as modified from March, S. et al. Anal. Biochem. 60: 149(1974) was applied to the preparation of specific allergens using Reaction Sequence 2b and described herein:

(i) 124 nM of Matrix-OH as described under Scheme 1, supra, was dissolved in 2.0 mls of 2.0M sodium carbonate and reacted with 100 ul of cyanogen bromide solution (2 grams of CNBr crystals dissolved in 1.0 ml of acetonitrile) for two minutes at pH 11.0 and further reacted for another two minutes with 100 ul of the same cyanogen bromide solution.

(ii) Immediately thereafter 385 nM of amino acid copolymer was added to (i) above and allowed to react overnight at ambient temperature while stirring.

(iii) The reaction mixture was chromatographed on Sephacryl-300 column to isolate the Matrix-copolymer conjugate and further dialyzed against distilled water followed by dialysis against acetate buffer pH 5.0.

(iv) To the dialyzed Matrix-copolymer conjugate 20 mg of lyophilized allergen extract and 0.15M EDC were added and allowed to react for 24 hours at 4 degrees centigrade while maintaining the pH of the reaction mixture to pH 5.0. This was followed by dialyzing the reaction mixture containing the Matrix-copolymer-allergen conjugate against 0.1M sodium bicarbonate pH 8.1 for 12 hours at 4 degrees centigrade. The reaction sequence here follows that described under Example 1 at reaction step (vi). The alternate reaction using biotinylated polylysine is also the same as in Example 1, supra.

REACTION SEQUENCE 3a 1,4-Butanedioldiglycidyl Ether (BDDGE) Activation and Coupling

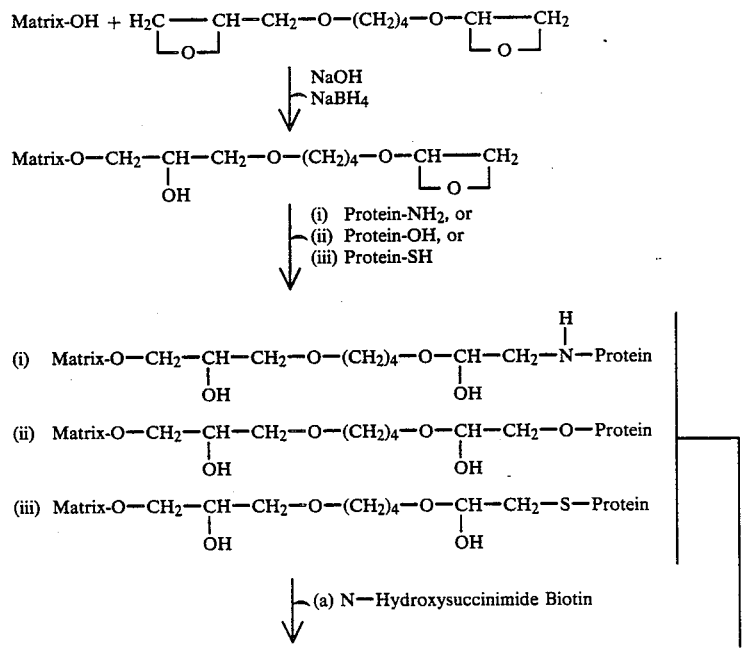

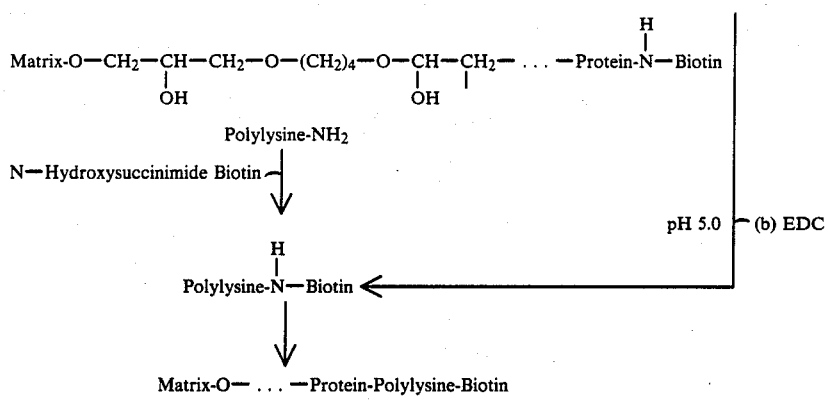

REACTION SEQUENCE 3b
Use of Amino Acid Copolymer with BDDGE Reaction

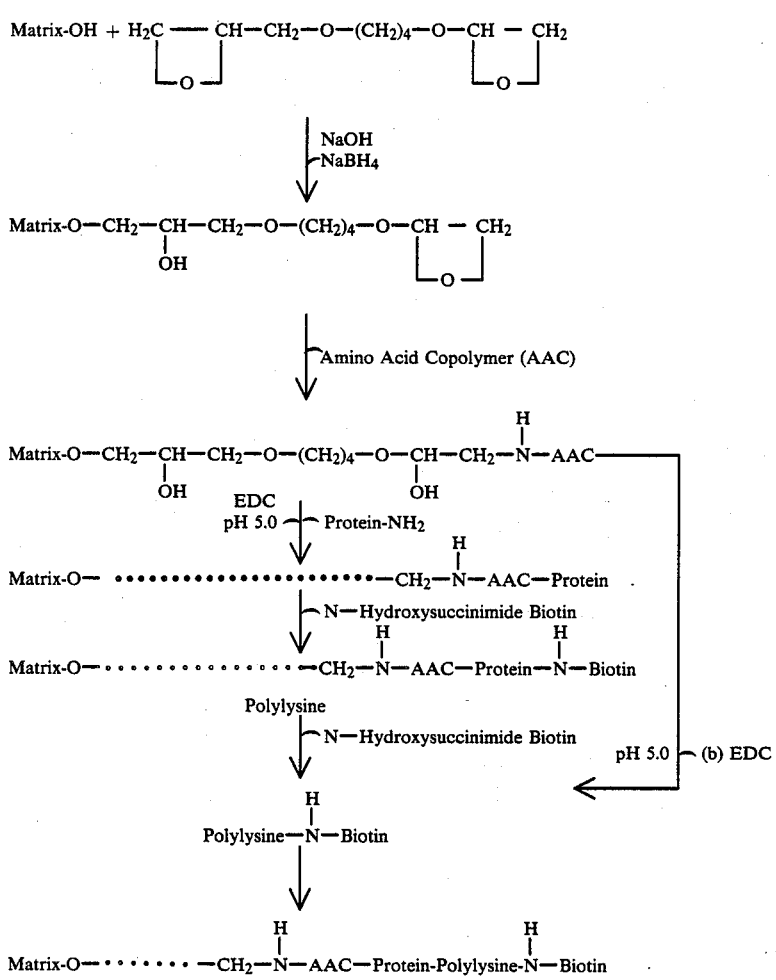

EXAMPLE 3
Preparation of Matrix Containing Specific Allergens Using Reaction Sequence 3b The above BDDGE activation reaction as modified from Sunberg, L. et al. J. Chromatography, 90: 87 (1974) was applied to the preparation of specific allergens using Reaction Sequence 3b and described herein:

(i) 150 nM of Matrix-OH as described under Reaction Scheme 1 was dissolved in 4.0 mls of 0.3M sodium hydroxide containing 0.26 mM sodium borohydride and reacted with 2.7 mM of 1,4-butanedioldiglycidyl ether for 4 hours at ambient temperature.

(ii) To the activated Matrix in (i) above 600 nM of amino acid copolymer was added and further reacted for 4 hours at 4 degrees centigrade. The reaction mixture was then dialyzed against distilled water and further dialyzed against acetate buffer pH 5.0

(iii) To the resultant Matrix-copolymer conjugate 20.0 mg of lyophilized allergen extract and 0.15M EDC was added as in reaction step (v). The reaction sequence follows that of Example 1 at reaction step (vi). The alternate biotinylated polylysine reaction sequence is also the same as in Example 1, supra.

REACTION SEQUENCE 4

Carboxymethylation Reaction

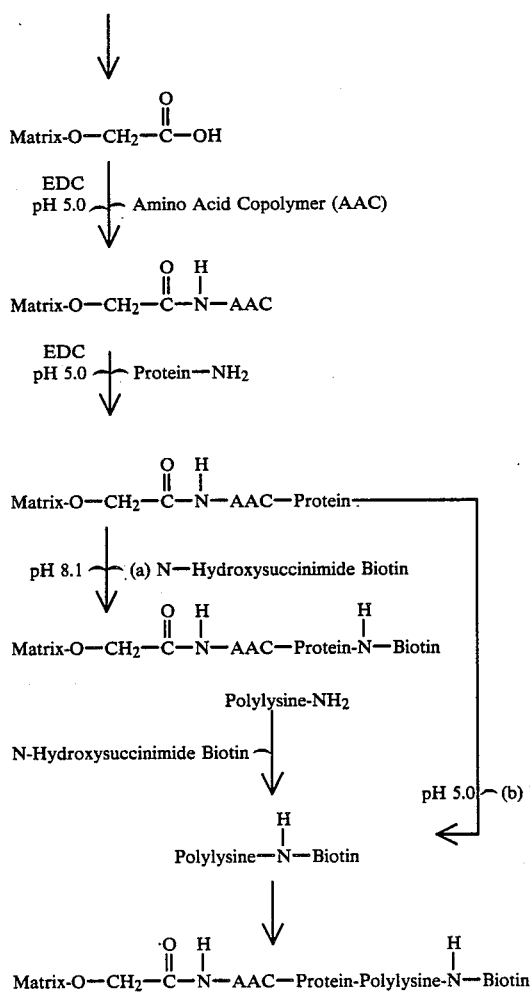

EXAMPLE 4

Preparation of Matrix Containing Specific Allergens Using Reaction Sequence 4

The carboxymethylation activation reaction as modified from Inman, J. J. Immunol. 114: 704 (1975) was applied to the preparation of specific allergens using Reaction Sequence 4 and described herein:

(i) 0.33 uM of Matrix-OH as described under Reaction Scheme 1 was dissolved in 0.32 mls of 1.35M sodium chloroacetate (300 mls of distilled water + 135 mls of 5M sodium hydroxide + 64.4 grams of chloroacetic acid; pH adjusted to 6.8 and final volume adjusted to 500 mls with distilled water). This mixture was mixed for few minutes very vigorously.

(ii) 86 ul of 10M sodium hydroxide was added and the volume adjusted to 0.43 mls with distilled water and allowed to react for 3 hours at 40 degrees centigrade.

(iii) 17.2 ul of 2.0M sodium phosphate monobasic was added to the reaction mixture which was titrated to pH 7.0 using 0.1M hydrocloric acid. The activated matrix was then dialyzed against distilled water followed by further dialysis against acetate buffer pH 5.0.

(iv) The carboxymethyl-matrix was then reacted with 770 nM of amino acid copolymer in the presence of 0.15M EDC at pH 5.0 for 24 hours at 4 degrees centigrade. The reaction mixture was then dialyzed against distilled water followed by dialysis against acetate buffer pH 5.0.

(v) 20 mg of specific lyophilized allergen was added together with 0.15M EDC to the Matrix-copolymer conjugate in step (iv) and allowed to react as in Example 1 reaction step (v). The reaction sequence follows that of Example 1 reaction step (vi) and the alternate reaction using biotinylated polylysine is the same as in Example 1, supra.

REACTION SEQUENCE 5a
Periodate Reaction
REACTION SEQUENCE 5b
Use of Amino Acid Copolmer with Periodate Reaction
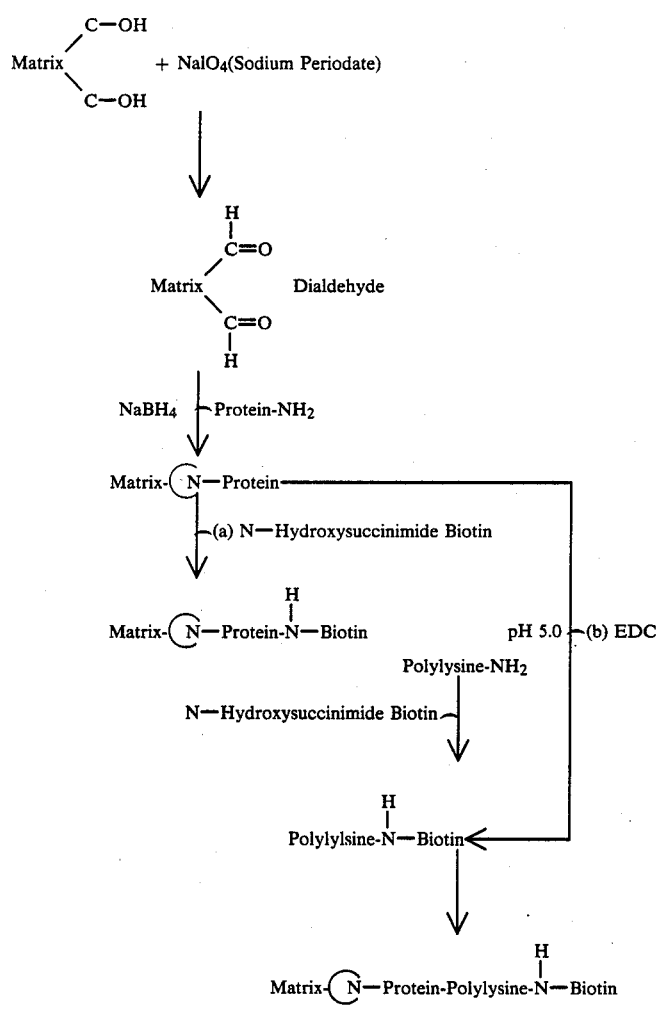
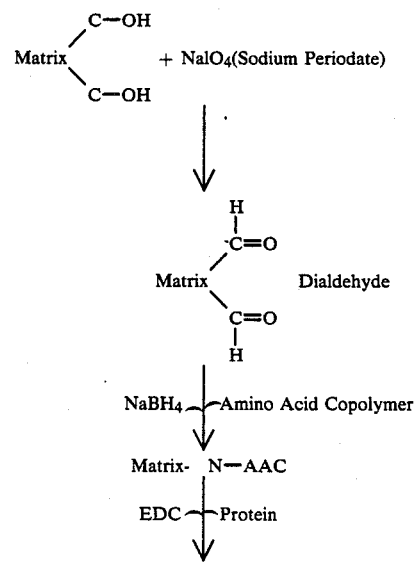

-continued

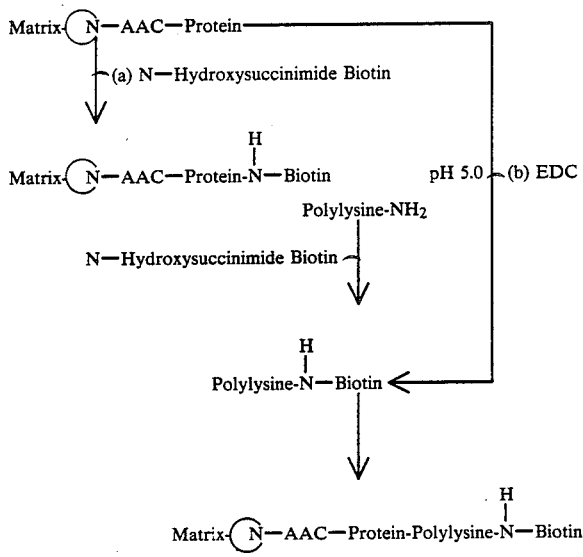

EXAMPLE 5

Preparation of Matrix containing Specific Allergens using Reaction Sequence 5

The above periodate activation reaction as modified from Nakane, P. et al. J. Histochem. Cytochem. 22: 1084 (1974) was applied to the preparation of specific allergens using Reaction Sequence 5b and described herein:

(i) 124 nM of Matrix-OH as described under Reaction Scheme 1 was dissolved in 0.3M sodium bicarbonate at pH 8.1 and reacted with 1.0 ml of 0.2M sodium periodate for one hour at ambient temperature.

(ii) 500 nM of amino acid copolymer was added and reacted for 150 minutes at ambient temperature. 0.26 mM of sodium borohydride was added to stabilize the Schiff's base.

(iii) The Matrix-copolymer conjugate was dialyzed against distilled water and further dialyzed against acetate buffer pH 5.0. The reaction sequence then follows the same steps as in Example 1 reaction step (v) through reaction step (vi) and the alternate biotinylated polylysine reaction follows that of Example 1, supra.

REACTION SCHEME II

Soluble polymers are used in this reaction scheme: (i) polyacrylic acid with a molecular mass varying from 5,000 to 120,000 daltons, (ii) 50% to 100% carboxylated polyacrylamide with a molecular mass varying from 120,000 to 240,000 daltons and (iii) polypeptides or copolymers exhibiting reactive carboxyl groups varying in molecular mass from 5,000 to 200,000 daltons. The reaction sequence for these forms of polymers and copolymers are similar.

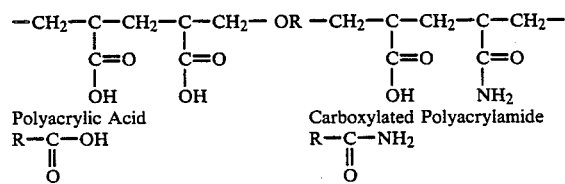

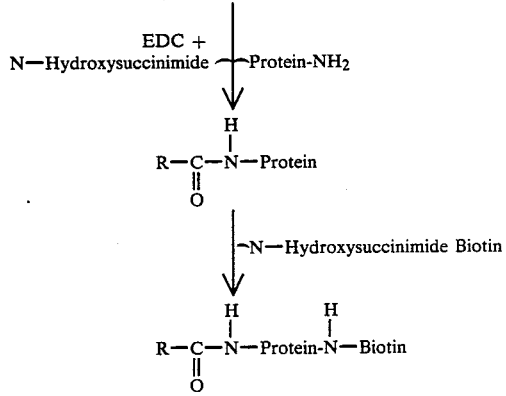

EXAMPLE 6

Preparation of Matrix Containing Specific Allergens Using Reaction Scheme II (i) 0.033 nM of polyacrylic or carboxylated polyacrylamide was dissolved in 2.0 mls of 0.01M phosphate buffer pH 8.0. 0.1M of each EDC and N-hydroxysuccinimide were added to the polymer solution followed by the addition of 10.0 mg of lyophilized specific allergen extract and incubated for 24 hours at ambient temperature while maintaining the pH at 8.0

(ii) The polymer-allergen conjugate was chromatographed on a Sehadex G-100 column and eluted with 0.01M phosphate buffer pH 7.5 and the exclusion volume collected.

(iii) The exclusion volume collected was concentrated to 2.0 mls by centrifugal evaporation and reacted with 0.73 mM of N-hydroxysuccinimide biotin for 2 hours at ambient temperature.

(iv) The polymer-allergen-biotin conjugate was dialyzed against 0.01M phosphate buffer pH 7.5 for 18 hours at 4 degrees centigrade.

CHOICE OF LIGAND AND ANTI-LIGAND CONFIGURATION

Specific ligands and their anti-ligand counterparts that can be used in the context of the present invention are selected from a host of different compounds. Examples shown here are illustrative only and the use of any other ligand-anti-ligand combination will be obvious to those skilled in the art.

| Ligand | Anti-ligand |
|---|---|
| Hapten | Anti-hapten |
| Biotin | Avidin |
| Fluoresceine | Anti-fluoresceine |
| Dinitrophenol | Anti-dinitrophenol |
| Avidin | Anti-avidin |
| Biotin | Anti-biotin |
| Bovine serum Albumin | Anti-bovine serum albumin |

In the above examples of ligands and anti-ligands the reaction sequence as described herein is carried out in a reaction vessel, e.g., a test tube, then the solid phase support containing the anti-ligand is introduced into the same reaction vessel. The solid phase support in this case could be a coated bead, dip-stick, and the like.

It is desirable at times to use a coated tube solid phase support since it is easily handled and washed. In this case the above configuration may be unsuitable since the first reaction is conducted in the liquid phase followed by a solid phase separation. If a liquid first reaction is not sought then the above-mentioned ligand-anti-ligand combinations are suitable in the preparation of a solid phase matrix as described herein. If, on the other hand, a liquid phase first reaction is sought and if both reactions were to be conducted in the same reaction vessel, like, for example, a coated tube, then several possible configurations are here sought for such an application:

(1) The ligand attached to the liquid matrix is avidin and the solid phase coated tube is coated with avidin. To effect the immobilization of the immunocomplex matrix containing avidin onto the avidin coated tube, biotin is added after the initial liquid phase reaction has been completed. This will form the following immobilized complex:

MATRIX-... Avidin-Biotin-Avidin- ▤ as shown in Schemes I and II, supra.

(2) By biotinylating the liquid matrix as described previously and using an anti-avidin antibody on the coated tube solid phase, immobilization of the former onto the latter can be achieved by the addition of avidin, after the initial liquid phase reaction, to the reaction mixture which will bind to both the anti-avidin antibody and the biotinylated liquid immunocomplex matrix. This will form the following immobilized complex:

MATRIX... Biotin-Avidin-Anti-Avidin- ▤

(3) By biotinylating the liquid matrix as described previously and using a coated tube coated with biotinylated protein such as bovine serum albumin, immobilization of the former onto the latter is achieved by adding avidin to the reaction vessel after the initial liquid phase reaction has taken place. This will form the following immunocomplex on solid phase:

MATRIX... Biotin-Avidin-Biotin-BSA-▤

Other possible combinations are obvious to those skilled in the art.

EXAMPLE 7

The Determination of Circulating Total IgE (Reagin Immunoglobulins) by the Present Invention Two different monoclonal antibodies were raised against purified IgE and recognizing two different epitopes on the IgE molecule using the method of Galfre, G. and Milstein, C. (Preparation of Monoclonal Antibodies: Strategies and Procedures. In Methods of Enzymology, Immunochemical Techniques, vol. 73, Langone, J. and Van Vunakis, H., eds. Academic Press (1981) pp. 3–46).

The IgG fraction from each antibody was purified on the DEAE-Sepharose CL-6B after ammonium sulfate precipitation. One antibody was conjugated to horse radish peroxidase enzyme using the periodate method of Nakane, P. et al., J. Histochem. Cytochem. 22: 1084 (1974) and diluted to a working solution in 0.05M phosphate buffer pH 7.0 containing 0.15M sodium chloride, 0.01% thimerosal and 0.1% human serum albumin. The second monclonal antibody for IgE was attached to polyacrylic acid and further biotinylated as described under Reaction Scheme II, Example 6, supra, using 2.94 nmoles of purified IgG in place of the specific allergen as described under Example 6. The polyacrylic acid-anti-IgE-biotin complex was diluted to a working solution in the same buffer as the enzyme label described above.

Avidin was passively immobilized on a one-eighth inch polystyrene bead using the method of Catt, K. and Tregear, G. W. Science 158: 1570 (1967) and further lyophilized to remove excess moisture.

Standards having IgE values ranging from 10 to 600 IU/ml were prepared in horse serum and standardized against the World Health Organization's Second International Reference Preparation for Human Serum IgE, number 75/502.

Total circulating IgE in 30 serum samples chosen randomly were determined as follows:

10 ul of each of the IgE standards including a zero standard and 10 ul of each serum sample were pipeted into a 12×75 mm test tube. To each tube 100 ul of the polyacrylic acid-anti-IgE-biotin complex and 100 ul of the enzyme labeled monoclonal anti-IgE antibody were added and the tubes mixed briefly and incubated for 30 minutes at ambient temperature. After this initial incubation one avidin coated bead was added to each tube and all tubes further incubated for another 30 minutes while shaking at ambient temperature. The beads were subsequently washed twice with the same buffer used for the monoclonal antibodies but containing 0.5% Tween-20 and reacted for 10 minutes with 0.5 ml of enzyme substrate containing 3.5 mg of hydrogen peroxide and 5.0 mg of o-phenylenediamine in 0.1M citrate-phosphate buffer pH 5.0. The color reaction was stopped by adding 0.5 ml of 0.5M sulfuric acid and the color absorbance determined on a spectrophotometer set at a wavelength of 492 nm. The absorbance of each point on the standard curve are tabulated below as follows:

| IgE. IU/ml | Absorbance |
|---|---|
| 0 | 0.010 |
| 10 | 0.051 |
| 30 | 0.106 |
| 100 | 0.313 |
| 300 | 0.809 |
| 600 | 1.370 |

The IgE concentration in each of the 30 serum samples was computed from the above standard curve and compared to the IgE concentration determined on the same samples using Pharmacia's Inc. (Piscataway, N.J.) total IgE enzyme assay with the following regression results:
Mean Pharmacia: 89 IU/ml
Mean Present Method: 88 IU/ml
Present Method=1.04 Pharmacia-2.7 IU/ml
Correlation Coefficient=0.9690

EXAMPLE 8

Determination of IgE Specific Allergens Using the Present Invention

The determination of IgE specific allergens was conducted using the embodiments of the present invention and assayed according to the following protocol:

200 ul of Matrix-allergen-biotin or Matrix-allergen-AAC-biotin or Matrix-allergen-AAC-polylysine-biotin in 0.05M phosphate buffered saline pH 7.0 as described under Example 7 above were added to 100 ul of patient serum or atopic calibrator and allowed to react for 2 hours at ambient temperature. One avidin coated bead was added to each tube and the reaction allowed to continue for 60 minutes at ambient temperature on a mechanical shaker set at 200 strokes per minute. The beads were washed twice as described under Example 7 above and reacted for another 60 minutes at ambient temperature with 300 ul of goat anti-IgE-horse radish peroxidase enzyme label diluted in same buffer as above. The beads were re-washed twice and further reacted for 20 minutes with 300 ul of enzyme substrate as described under Example 7 above and the reaction stopped with 0.5 ml of 0.5M sulfuric acid and the color absorbance was recorded at 492 nm.

The following results were obtained on a selected group of allergens attached to different matrices as described under Reaction Schemes I and II, supra:

(a) Timothy Grass. G6:

Purified Timothy grass (G6) was attached to (i) Ficoll 70 through polyglutamic, glutamic ester as described under Example 1 of Reaction Sequence 1b, (ii) polyacrylic acid (PAA) as described under Example 6 and (iii) carboxylated polyacrylamide (CPA) as described under Example 6. A Class IV atopic serum for G6 as classified by the Phadebas-RAST kit from Pharmacia (Piscaway, N.J.) was diluted in a non-atopic serum to simulate atopic Classes III, II and I and were assayed using the above protocol along with four other atopic samples and one non-atopic sample with the following results recorded:

| | MATRIX: | | |
|---|---|---|---|
| | Ficoll 70 | PAA | CPA |
| | | Absorbance | |
| Class IV | 1.660 | 1.630 | 1.765 |
| Class III | 0.403 | 0.500 | 0.557 |
| Class II | 0.157 | 0.174 | 0.253 |
| Class I | 0.091 | 0.087 | 0.121 |
| Non-Atopic Serum | 0.041 | 0.020 | 0.035 |
| Patient # | | | |
| 1 | 1.783 | 2.878 | 2.753 |
| 2 | 0.534 | 0.637 | 0.955 |
| 3 | 1.036 | 1.232 | 1.163 |
| 4 | 0.434 | 0.441 | 0.409 |

(b) Birch Tree:

Purified Birch Tree allergen extract (T3) was attached to (i) Ficoll 70 through the amino acid copolymer polylysine, phenylalanine as described under Example 1 using Reaction Sequence 1b, supra, (ii) Dextran 80 through polyglutamic, alanine, lysine, tyrosine copolymer as described under Example 2 using Reaction Sequence 2b, supra and (iii) carboxylated polyacrylamide (CPA) as described under Example 6 of Reaction Scheme II, supra.

A Class IV atopic serum for T3 as classified by the Phadebas-RAST kit of Pharmacia was diluted with a non-atopic serum to simulate atopic Classes III, II and I and were assayed using the above protocol along with two atopic sera and one non-atopic serum for T3 with the following results recorded:

| | MATRIX: | | |
|---|---|---|---|
| | Ficoll 70 | Dextran 80 | CPA |
| | | Absorbance | |
| Class IV | 1.066 | 1.126 | 2.430 |
| Class III | 0.239 | 0.242 | 0.979 |
| Class II | 0.105 | 0.112 | 0.313 |
| Class I | 0.075 | 0.082 | 0.178 |
| Non-Atopic Serum | 0.045 | 0.062 | 0.026 |
| Patient # | | | |
| 1 | 0.732 | 1.317 | 1.041 |
| 2 | 0.571 | 1.102 | 1.990 |

The choice of matrix, copolymer and the reaction scheme and sequence to be used for a given allergen will depend of the protein content of each allergen and will be obvious to those skilled in the art.

Having described the invention, it is intended that it be limited only by the lawful scope of the appended claims.

We claim:

1. A method for measuring the level of an antigen ($Ag_1$), antibody ($Ab_1$) or hapten (H) in a liquid sample, which sequentially comprises:

(a) forming in a liquid phase reaction a soluble complex wherein said antigen ($Ag_1$), antibody ($Ag_1$) or hapten (H) is linked through, respectively, a specific antibody (Ab), antigen (Ag) or anti-hapten (Anti-H), to a matrix which is soluble in the liquid phase and carries a ligand (X), said matrix capable of being chemically attached to more than one specific antibody (Ab), antigen (Ag) or anti-hapten (Anti-H);

(b) forming an insolubilized complex comprising a solid support linked to the ligand (X) of said soluble complex through an anti-ligand (Y), the insolubilized complex carrying a label (Z) linked to the antigen ($Ag_1$) through an anti-antigen (Anti-$Ag_1$), to the antibody ($Ab_1$) through an anti-antibody (Anti-$Ab_1$) or to the hapten (H);

(c) washing the insolubilized complex; and (d) observing the washed insolubilized complex for the presence of the label (Z) wherein the presence of the label (Z) is an indication of the level of said antigen ($Ag_1$), antibody ($Ab_1$) or hapten (H) in said sample.

2. A method according to claim 1 wherein the label (Z) is an enzymatic label, a radioactive label, a fluorescent label, chemiluminescent label or a bioluminescent label.

3. A method according to claim 1 or 2 wherein the matrix is a soluble carbohydrate with a molecular mass of from 6,000 to 80,000 daltons or a Ficoll with a molecular mass of from 70,000 to 400,000 daltons.

4. A method according to claim 3 wherein the matrix is a dextran.

5. A method according to claim 1 or 2 wherein the matrix is a soluble polymer or copolymer with a molecular mass of from 5,000 to 200,000 daltons.

6. A method according to claims 1 or 2 wherein the ligand (X) is covalently attached to the matrix through an amino acid copolymer.

7. A method according to claims 1 or 2 wherein the ligand (X) is avidin, the solid support is a tube coated with avidin, and biotin is added to effect the immobilization of the soluble complex onto the avidin coated tube.

8. A method according to claims 1 or 4 wherein the ligand (X) is biotin, the solid support is a tube coated with an anti-avidin antibody, and avidin is added to effect the immobilization of the soluble complex onto the anti-avidin antibody coated tube.

9. A method according to any one of claims 1 to 6 wherein the ligand (X) is biotin, the solid support is a coated tube coated with biotinylated protein, and avidin is added to effect the immobilization of the soluble complex onto the biotinylated protein coated tube.

10. A method according to claims 1 or 2 wherein the ligand (X) is selected from hapten, avidin and bovine serum albumin, and the anti-ligand (Y) is selected from anti-hapten, anti-avidin and anti-bovine serum albumin, respectively, and wherein the hapten is selected from biotin, fluoresceine and dinitrophenol, and the anti-hapten is selected from avidin or anti-biotin, anti-fluoresceine and anti-dinitrophenol, respectively.

11. A method according to claims 1 or 2 wherein the ligand (X) is covalently attached to the matrix, and the specific antibody (Ab) or antigen (Ag) is chemically attached to the matrix.

12. A method according to claims 1 or 2 wherein the sample contains an antigen ($Ag_1$) or antibody ($Ab_1$), the soluble complex is formed by reacting the sample in the liquid phase with said matrix carrying ligand (X) and specific antibody (Ab) or antigen (Ag) in the presence of an anti-antigen (Anti-$Ag_1$) or anti-antibody (Anti-$Ab_1$) labelled with said label (Z) to form said soluble complex, reacting this soluble complex with immobilized anti-ligand (Y) on a solid support to form an insolubilized complex, washing the insolubilized complex, and observing the washed insolubilized complex for the label (Z) on the anti-antigen (Anti-$Ag_1$) or anti-antibody (Anti-$Ab_1$).

13. A method according to claims 1 or 2 wherein the sample contains an antigen ($Ag_1$) or antibody ($Ab_1$), the soluble complex is formed by reacting the sample in the liquid phase with a said matrix carrying said ligand (X) and said specific antibody (Ab) or antigen (Ag), the insolubilized complex is formed by contacting said soluble complex with immobilized anti-ligand (Y) on a solid support to form an insolubilized complex, washing the insolubilized complex, reacting it with an anti-antigen (Anti-$Ag_1$) or anti-antibody (Anti-$Ab_1$) labelled with said label (Z), rewashing the resulting insolubilized complex, and observing the washed insolubilized complex for the presence of the label attached to the anti-antigen (Anti-$Ag_1$), or anti-antibody (Anti-$Ab_1$).

14. A method according to claims 1 or 2 wherein the sample contains a hapten (H), the soluble complex is formed by reacting the sample in the liquid phase with a said matrix carrying ligand (X) and a specific anti-hapten (Anti-H) in the presence of a labeled hapten probe (H-Z), allowing competitive binding to occur between the hapten (H) in the sample and the labeled hapten probe (H-Z) for anti-hapten (Anti-H) binding sites on the matrix, reacting the resulting soluble complex with immobilized anti-ligand (Y) on a solid support to form an insolubilized complex, washing insolubilized complex, and observing the washed insolubilized complex for the label (Z).

* * * * *